(12) United States Patent
Echarri et al.

(10) Patent No.: US 6,278,258 B1
(45) Date of Patent: Aug. 21, 2001

(54) IMPLANTABLE POWER MANAGEMENT SYSTEM

(75) Inventors: Guillermo Echarri; Roberto Echarri, both of Miami; Francisco Jose Barreras, Sr., Miami Beach; Oscar Jimenez, Coral Gables, all of FL (US)

(73) Assignee: Exonix Corporation, Miami, FL (US)

( * ) Notice: Subject to any disclaimer, the term of this patent is extended or adjusted under 35 U.S.C. 154(b) by 0 days.

(21) Appl. No.: 09/649,918

(22) Filed: Aug. 30, 2000

Related U.S. Application Data (62) Division of application No. 09/299,858, filed on Apr. 26, 1999.

(51) Int. Cl.[7] .................................................. H01M 10/46
(52) U.S. Cl. ............................................. 320/130; 320/160
(58) Field of Search .................................... 320/106, 116, 320/124, 125, 131, 130, 132, 134, 135, 160, 161, 162, 163, 164, 127

(56) References Cited

U.S. PATENT DOCUMENTS

| | | |
|---|---|---|
| 5,411,537 | 5/1995 | Munshi et al. . |
| 5,534,765 | 7/1996 | Kreisinger et al. . |
| 5,631,537 | 5/1997 | Armstrong . |
| 5,670,862 | 9/1997 | Lewyn . |
| 5,675,235 | 10/1997 | Nagai . |
| 5,764,030 | 6/1998 | Gaza . |
| 5,811,959 | 9/1998 | Kejha . |
| 5,818,199 | 10/1998 | Beard . |
| 5,880,576 | 3/1999 | Nagai . |

*Primary Examiner*—Edward H. Tso
(74) *Attorney, Agent, or Firm*—Thomas R. Vigil (57) ABSTRACT

The method and system for managing power supplied from a charging circuit to a power source in an implantable medical device comprises the steps of and circuitry for: measuring the current drain of the medical device; measuring the elapsed time since the last full charge of a power source of the device; calculating the actual capacity of the power source (corrected for fade) based on the variable of current drain and the variable of elapsed time; calculating the operating time based on the variable of current drain and the variable of the actual capacity of the power source; measuring the voltage of the power source; signaling the medical device when the power source voltage has reached a certain low value which requires disconnection from the power source; disconnecting, during discharging, the power source from the medical device upon the power source reaching a certain low voltage in order to prevent deep discharging of the power source and subsequent damage; precisely limiting the charging voltage to the power source in order to prevent overcharging beyond safe limits; disconnecting, during charging, the power source from the charging circuit upon the power source reaching a certain high voltage in order to prevent overcharging of the power source and subsequent damage; sensing when the electromagnetic waves being transmitted by an RF transmitter/charger induce a voltage level above a certain value at an RF receiver of the implanted power management system; reconnecting power supply inputs of the medical device to the power source upon sensing this induced high voltage level; monitoring the temperature of the power source during charging and discharging; disconnecting the charging circuitry from the power source if the temperature of the power source raises above a certain level during charging; reconnecting the charging circuitry to the power source when the temperature of the power source drops below a certain low value during charging; disconnecting the implanted medical device from the power source if the temperature of the power source raises above a certain level during discharging; and, reconnecting the medical device to the power source when the temperature of the power source drops below a certain low value during discharging.

22 Claims, 5 Drawing Sheets

IMPLANTABLE POWER MANAGEMENT SYSTEM

This application is a Div of Ser. No. 09/299,858 Apr. 26, 1999.

BACKGROUND OF THE INVENTION

1. Field of the Invention

The present invention relates to a method and circuitry for safely regulating the charge and discharge cycles of implantable grade, rechargeable power sources, utilizing inductively coupled radio frequency energy. Patient safety and power source longevity are vastly improved by the method and circuitry of the system of the present invention. Such safety and longevity are obtained by the steps of: (1) measuring and recording, each charge/discharge cycle, to obtain the corrected capacity of the power source in order to calculate and display, upon interrogation, the remaining operating time of the implanted device, (2) providing within the implanted medical device circuitry for disconnecting the power source upon reaching a pre-selected low voltage in order to prevent deep-discharging the power source below safe limits, (3) providing circuitry for using variable constant current charge rates, (4) providing circuitry for switching to constant voltage to top-off the power source at the completion of the charge cycle, in order to prevent overcharging beyond safe limits, (5) providing within the implanted medical device circuitry for disconnecting the charging circuit from the power source upon the power source reaching a preselected high voltage level, (6) providing circuitry for full-time RF powered operation, in case of failure of the internal power source or for operation of the implanted medical device requiring extremely high power consumption (rather than being powered from the internal power source of the implanted device), (7) providing circuitry for transmitting to a remote receiver, via a telephone link, critical data that can be used by the physician and/or the device manufacturer to assess the performance and condition of the rechargeable power source and the Implantable Medical Device, and (8) providing circuitry for transmitting to the implantable medical device, via a telephone link, new operation parameter value(s).

2. Description of the Prior Art

A number of new, state-of-the-art, implantable medical devices are powered by a rechargeable electrical power source, such as a small volume, large value capacitor (known as a Super-capacitor), or a rechargeable electrochemical cell. These power sources need to be periodically recharged by an external Radio Frequency (RF) Transmitter via inductive coupling in a manner known in the art.

Each type of power source has a different charge and discharge methodology which must be faithfully followed to prevent permanent damage to the power source. In the prior art, the charge/discharge methodology has been factory preset via a specific hardware circuitry, suitable only for the specific power source used to power the implantable device. Furthermore, the prior art circuitry is incapable of properly regulating the charge/discharge cycles of new implantable-grade power sources, such as a Lithium-Ion cell battery.

Heretofore various battery power source charging systems have been proposed. Examples of some of these previously proposed systems are disclosed in the following U.S. patents:

| U.S. Pat. No. | Patentee |
|---|---|
| 5,411,537 | Munshi et al. |
| 5,631,537 | Armstrong |
| 5,670,862 | Lewyn |
| 5,675,235 | Nagai |
| 5,764,030 | Gaza |
| 5,811,959 | Kejha |
| 5,818,199 | Beard |
| 5,880,576 | Nagai |

SUMMARY OF THE INVENTION

The present invention provides the method, software and hardware to (a) support the correct charge/discharge regimen for different types of power sources, (b) the capability of selecting, via software, the correct regimen of current and voltage limits, and (c) the capability of non-invasively up-grading the regimen, by down-loading, via a direct telemetry link or telephone link, new software revisions incorporating new improvements.

Some new state-of-the-art implantable medical devices are powered by a rechargeable Super-capacitor. One limitation of a capacitive power source is the small amount of charge that it can hold relative to an electrochemical rechargeable cell. In the case of a Super-capacitor powered Implantable Medical Device, when the device requires very high power consumption, its power source must be recharged very frequently. This makes the Super-capacitor impractical as a power source for use in high power consumption implantable medical devices. One obvious solution is to replace the Super-capacitor with an electrochemical cell. However, most implantable-grade, rechargeable electrochemical cells exhibit other critical limitations when used in a hermetically sealed implantable unit. These limitations must be surmounted during the design phase of the charge/discharge regulating circuit for the implanted power source.

One of the power sources most suitable for use in hermetically sealed, rechargeable implantable medical devices, is the Lithium-Ion cell. It offers many advantages, such as relatively high energy density (high capacity), no outgassing during charge and discharge, high current delivery capabilities and relatively high output voltage. However, it also has some disadvantages, such as some loss of capacity with each recharge cycle (called "fade"), and the cell may be permanently damaged if allowed to be deeply discharged or overcharged. The continual loss of capacity (fade), requires the capability of measuring and up-linking (a) the corrected capacity value in mA-hrs, and (b) the power consumption of the Implanted Medical Device, in order to accurately calculate and display the operating time for the Implanted Medical Device. Having the capability of displaying the accurate operating time is extremely helpful to elderly patients for scheduling the next recharge session.

The power management system of the present invention provide a method and circuitry for measuring, on a real-time basis, the current power consumption and elapsed time since the last full charge. This data is used by a microcontroller to calculate (a) the actual capacity (corrected for fade) of the power source, and (b) the "operating time" for the Implantable Medical Device. This operating time can be up-linked by the Implantable Medical Device to the RF Transmitter/Charger where it can be displayed to the patient. Thus, the patent is provided, at any time, with an accurate prediction of the operating time as the cell's capacity slowly fades.

If desired, the work performed by the microcontroller in the power management system/module can be performed by a microcontroller of the Implantable Medical Device. In either event, the following functions are performed:

1. Detecting whether or not an RF sensor line has switched high or low.
2. Controlling the charging rate.
3. Non-invasively changing the charge high voltage limit.
4. Switching to a constant voltage mode to top off the charge on the power source.
5. Non-invasively changing the low voltage limit when the power source is disconnected during discharge.
6. Disconnecting the power source when it reaches the low voltage limit.
7. Reconnecting the power source upon sensing the transmission of RF energy.
8. Disconnecting the power source upon sensing a high temperature.
9. Reconnecting the power source when the temperature drops to a normal level.
10. Measuring the power consumption of the circuitry for the Implantable Medical Device.
11. Measuring the elapsed time since the last full charge.
12. Tracking the actual capacity of the power source.
13. Calculating the operating time left for the Implantable Medical Device.

It is an aspect or objective of the present invention to provide: (1) a method and circuitry for measuring the current drain of the Implantable Medical Device, (2) a method and circuitry for measuring the elapsed time since the last full charge, (3) a method for calculating the actual capacity of the power source (corrected for fade) based on the variable of current drain and the variable of elapsed time, (4) a method for calculating the operating time based on the variable of current drain and the variable of the actual capacity of the power source, (5) a method and circuitry for measuring the voltage of the power source, (6) a method and circuitry to signal the Implantable Medical Device when the power source voltage has reached a certain low value which requires disconnection from the power source, (7) a method and circuitry for disconnecting, during discharging, the power source from the Implanted Medical Device upon the power source reaching a certain low voltage in order to prevent deep discharging of the power source and subsequent damage, (8) circuitry for precisely limiting the charging voltage to the power source in order to prevent overcharging beyond safe limits, (9) a method and circuitry for disconnecting, during charging, the power source from the charging circuit upon the power source reaching a certain high voltage in order to prevent overcharging of the power source and subsequent damage, (10) circuitry for sensing when the electromagnetic waves being transmitted by the RF Transmitter/Charger induce a voltage level above a certain value at the RF Receiver of the Implanted Power Management System, (11) circuitry for reconnecting the power supply inputs of the Implanted Medical Device to the power source upon sensing this induced high voltage level, (12) a method and circuitry for monitoring the temperature of the power source during charging and discharging, (13) circuitry for disconnecting the charging circuitry from the power source if the temperature of the power source raises above a certain level during charging, (14) circuitry for reconnecting the charging circuitry to the power source when the temperature of the power source drops below a certain low value during charging, (15) circuitry for disconnecting the Implanted Medical Device from the power source if the temperature of the power source raises above a certain level during discharging, (16) circuitry for reconnecting the Implantable Medical Device to the power source when the temperature of the power source drops below a certain low value during discharging, (17) a method and circuitry for transmitting to a remote device, via a telephone link, data that can be used by the physician and/or the device manufacturer to assess the performance and condition of the rechargeable power source and the Implantable Medical Device, and (18) a method and circuitry for transmitting via a telephone link to, and setting in, the Implantable Medical Device, new operational parameter value(s).

DESCRIPTION OF THE PREFERRED EMBODIMENT(S)

Figure 1:
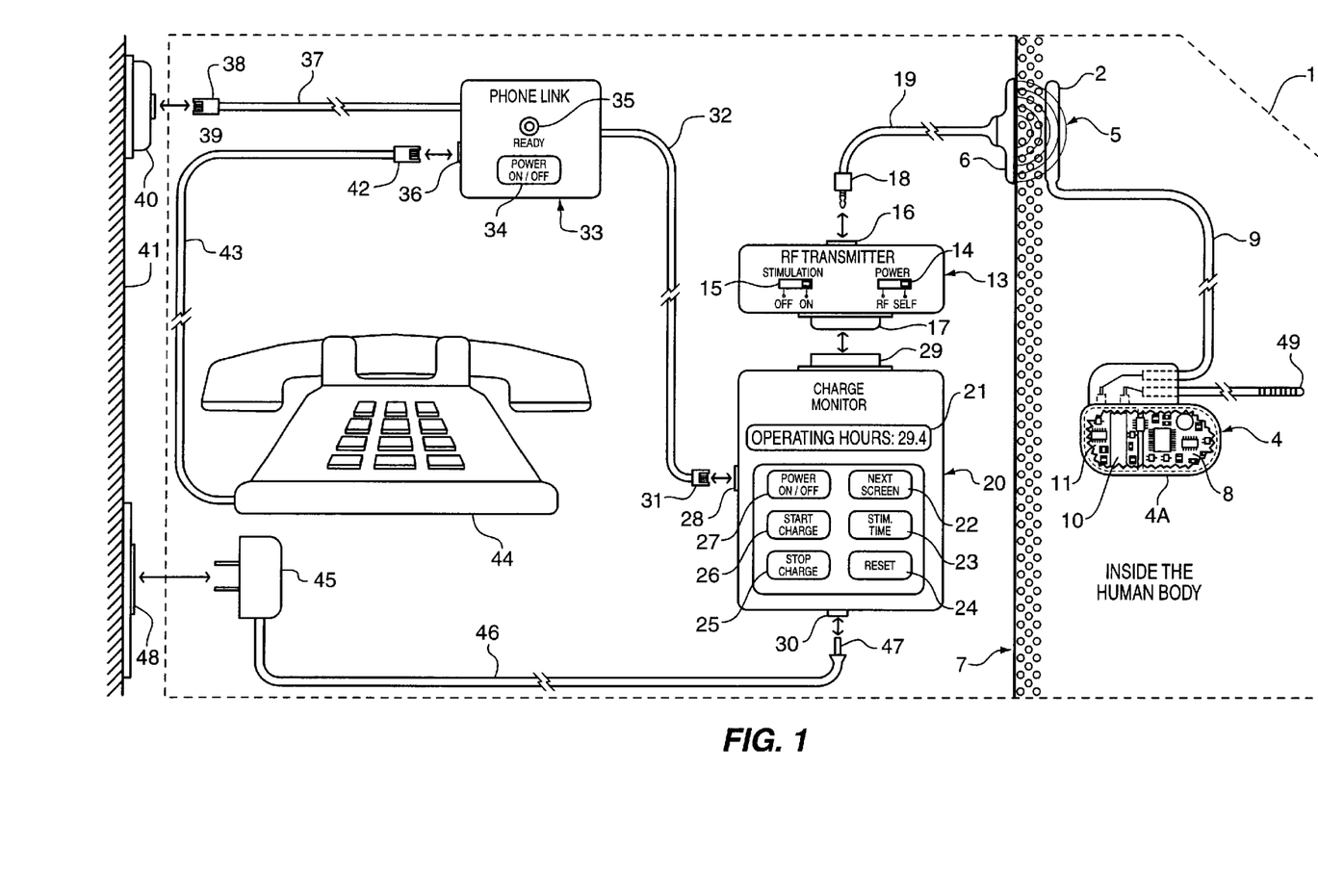
FIG 1 block plan view of one embodiment of the power management system of the present invention and shows a charge monitor, an RF transmitter, an Implanted Medical Device (Neural Stimulator) with exterior RF pick up coil and a telephone link.

FIG. 1 illustrates the power management system 1 of the present invention. The system 1 utilizes an implanted RF receiving antenna 2 located outside of an Implantable Medical Device 4. This RF receiving antenna 2 is used for capturing RF electrical energy 5 being transmitted by an RF Transmitting Antenna 6 located outside the human body tissue 7. The Implanted Medical Device 4 is typically enclosed in a hermetic titanium housing 4A in order to prevent intrusion of the body fluids which would permanently damage its sensitive electronic circuitry 8. This titanium housing 4A significantly attenuate and reduces the RF energy that can be coupled through the titanium enclosure 4A. Therefore, in FIG. 1, the RF receiving antenna 2 is placed outside of the Implanted Medical Device 4 but inside the human body, using insulated wires in a cable 9 to bring the coupled RF energy to the Implanted Medical Device 4 in order to recharge its power source 10.

Figure 2:
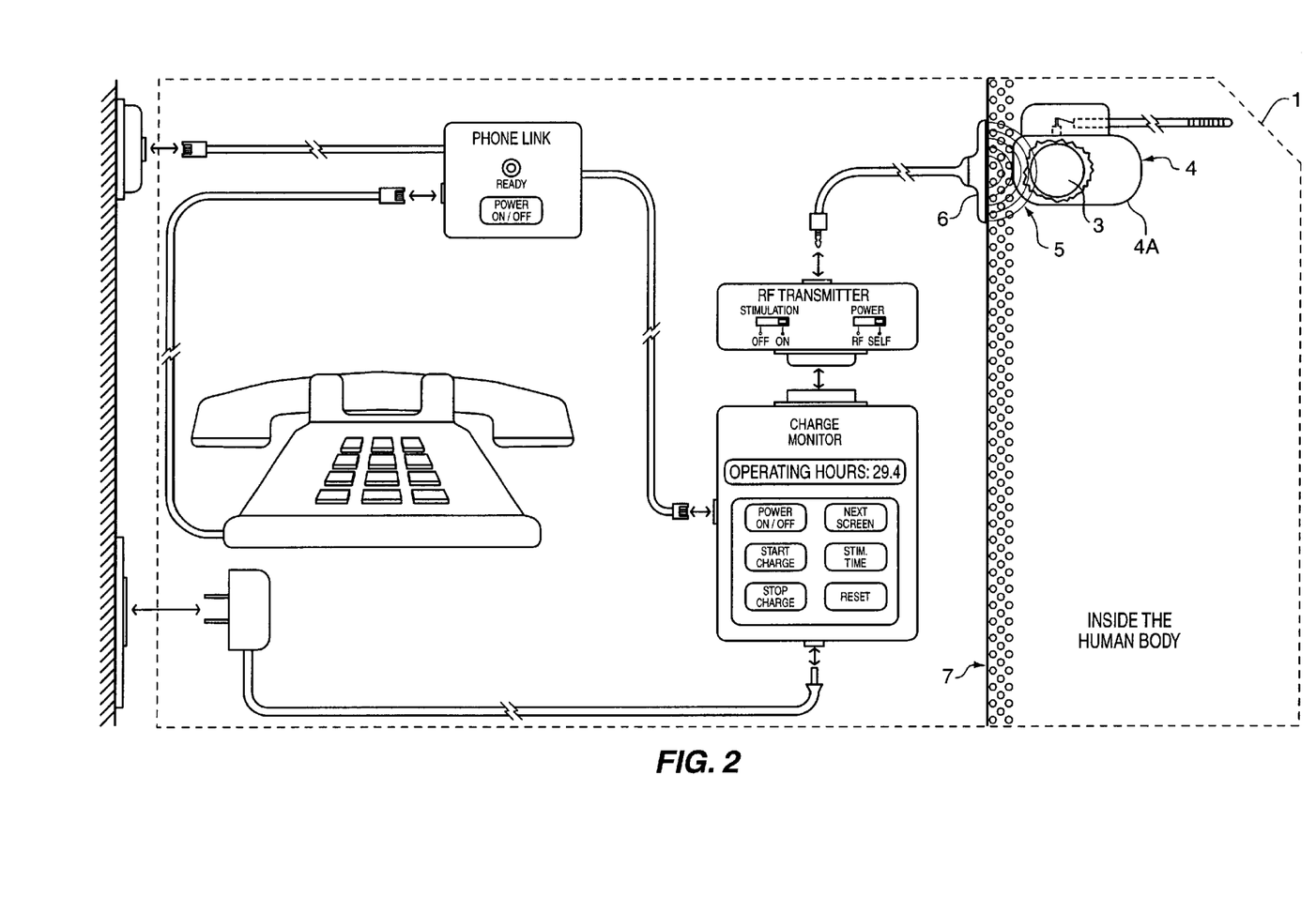
FIG. 2 block plan view of another embodiment of the power management system of the present invention, similar to the view shown in FIG. 1, and shows a charge monitor, an RF transmitter, an Implanted Medical Device (Neural Stimulator) without an exterior RF pick up coil and a telephone link.

FIG. 2 shows an embodiment of the Power Management System 1 without the external Rf antenna 2 and, instead, shows an RF receiving antenna 3 which is located inside of the Implantable Medical Device 4 for capturing the RF electrical energy 5 being transmitted by the RF transmitting antenna 6 located outside the human body. In this embodiment, a more compact Implantable Medical Device 4 is provided by placing the RF receiving antenna 3 inside the hermetic titanium enclosure 4A of the Implanted Medical Device 4. This compactness is achieved at the expense of reducing the amount of RF energy that can be coupled into the Implanted Medical Device 4. This requires transmitting substantially higher levels of RF energy, significantly decreasing the longevity of the battery powering an RF Transmitter Unit 13.

Figure 4:
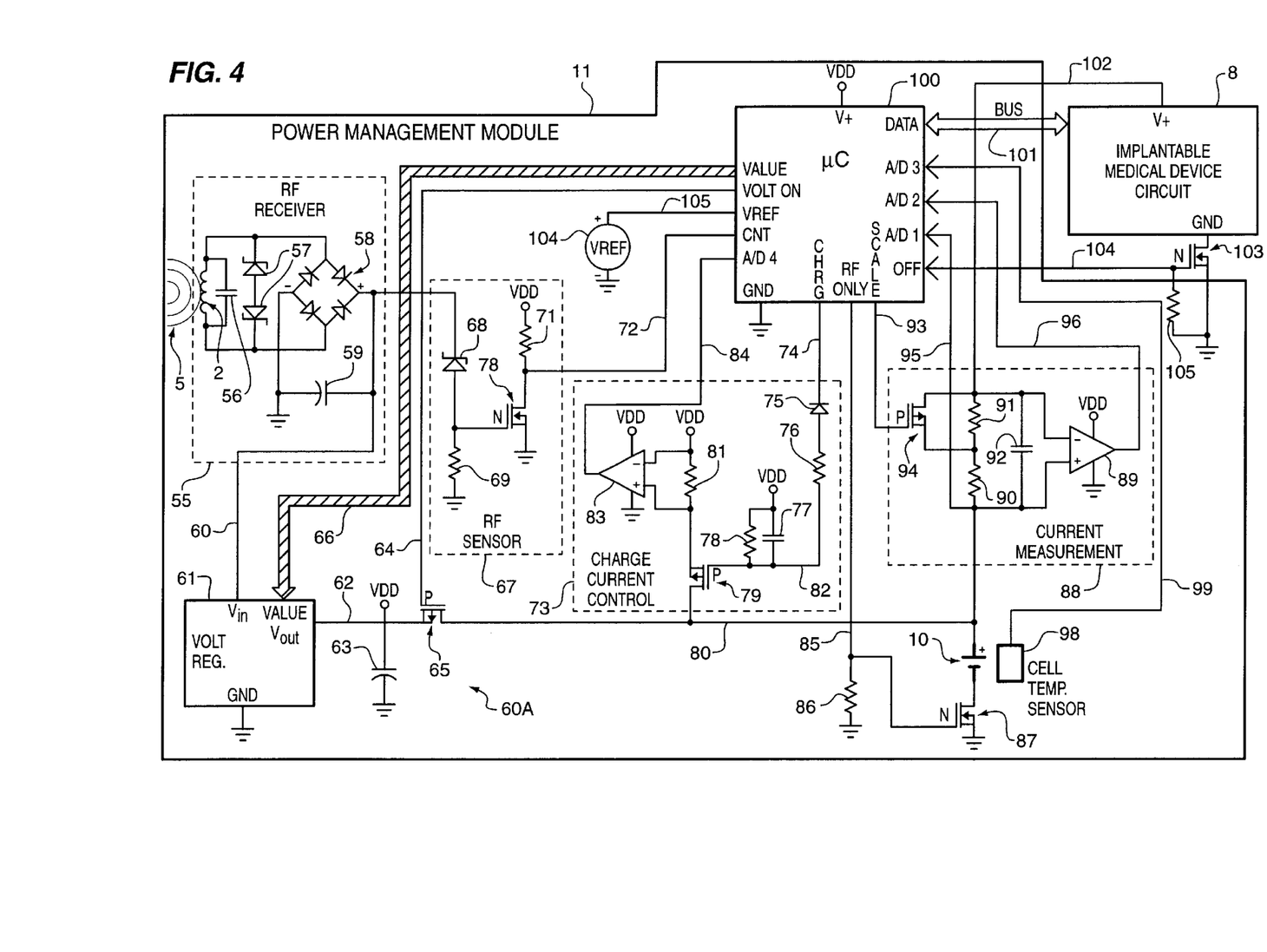
FIG. 4 is a block electrical schematic circuit diagram of the power management module located side the Implanted Medical Device.

FIG. 4 is a block schematic circuit diagram of the circuitry 8 for a Power Management System Module 11 located inside the Implanted Medical Device 4. The function of the Power Management Module 11 is to supervise the charging and discharging operations of the rechargeable power source 10 powering the Implantable medical Device 4, in order to improve the safety, efficacy and reliability of the rechargeable power source 10. This Power Management Module 11 incorporates distinctive circuitry and methods for operating same to: (a) sense when the RF energy coupled into the RF Receiver exceeds the minimum level for safe operation of the Implantable Medical Device, (b) adjust the rate of charge to the power source 10, (c) precisely regulate the voltage used to charge the power source, (d) non-invasively adjust the level of this charge voltage, (e) allow unidirectional current flow from the voltage regulator to the power source, (f) provide a low impedance path from the power source to the VDD connection supplying the operating power to a Power Management Module Controller 100 when the RF signal is not sensed, (g) sense the temperature of the power source, (h) disconnect the V— supply to the Implantable Medical Device 4 upon sensing a battery temperature which exceeds a safe value during discharging, (i) reconnect the V+ supply to the Implantable Medical Device upon the battery temperature dropping to a safe value during discharging, (j) disconnect a charging circuit 60A from the power source 10 upon sensing a battery temperature exceeding a safe value during charging, (k) reconnect the charging circuit 60A to the power source upon the battery temperature dropping to a safe value during charging, (l) disconnecting the charging circuit 60A from the power source upon sensing a "full" voltage level at the power source 10, (m) non-invasively adjust the value of this "full" voltage, and (n) reconnect the charging circuit 60A to the power source when the RF energy coupled into the RF Receiver exceeds the minimum level for safe operation of the Implantable Medical Device 4.

Referring again to FIG. 1, there is illustrated therein the main components of the Power Management System 1 used for maximum RF efficiency, where the RF receiving antenna 2 is placed outside the hermetic titanium enclosure 4A of the Implanted Medical Device 4. The Power Management System 1 is used to safely manage the charging and discharging of the power source 10 powering the Implantable Medical Device 4.

On the right half of FIG. 1, the main components of the Power Management System comprise: (a) Charge Monitor 20 which is used to display the "remaining operating time" and "corrected capacity" of the power source 10 powering the Implantable Medical Device 4, (b) an RF Transmitter Unit 13 used to generate the RF signal to be transmitted by antenna 6, (c) plug 18 which is used to connect the RF Transmitter Unit 13 to antenna 6, (d) RF Receiving Antenna 2 which is used to pick-up the RF energy 5 transmitted by antenna 6, (e) cable 9 which are used to bring inside the Implantable Medical Device 4 the induced RF energy, (f) Power Management Module 11 which is used to safely manage the charge/discharge cycles of the power source 10 powering the Implantable Medical Device 4 and to collect performance data, and (g) rechargeable power source 10 used to power the Implantable Medical Device.

RF Transmitter Unit 13 can be used as a stand-alone device when the Implantable Medical Device 4 must be powered full-time via RF coupled energy. When used for full-time RF power, a switch 14 must be switched to the "RF" position. When the Implantable Medical Device 4 is to be powered by its own rechargeable power source 10, RF Transmitter Unit 13 is used to generate the RF energy used to recharge the power source 10. In this case, the switch 14 of RF Transmitter Unit 13 must be switched to the "self" position and a plug 17 of RF Transmitter Unit 13 must be plugged into a jack 29 of the Charge Monitor 20. An A/C Transformer 45 can be used to power the Charge Monitor 20, or alternatively the Charge Monitor 20 can be powered by its own internal battery.

Referring to the Charge Monitor 20, a liquid crystal display 21 is used to display critical data, such as the "number of charge/discharge cycles" of the power source 10. Push button 22 is used to scroll the display 21 to the next data, such as the "corrected capacity" of the power source 10. The push button 22 "oper. time" is used to display the remaining operating time of the Implantable Medical Device 4 based on current power consumption and the present capacity of the power source 10. Push button 24 is used by the patient to return the Implantable Medical Device 4 to safe "default" parameter value(s) when newly programmed values via the Phone Link do not work correctly for the patient. Push button 25 is used to abort a charge cycle to the power source 10. Push button 26 is used to initiate a charge cycle for the power source 10. Push button 27 is used to power-up or power-down the Charge Monitor 20.

On the left side of FIG. 1, the remaining system components comprise: Phone Link coupler 33 which is used to convert digitally coded signals into audible distinctive "tones". These converted "tones" are sent to a standard telephone 44 via jack 30, plug 42 and cable 43. Note that data communications between Phone Link coupler 33, telephone 44 and the public telephone system is made via a cable 37, plug 38 and jack 39 of telephone wall plug 40. Also, note that data communications between Phone Link 33 and Charge Monitor 20 is made via a cable 32, plug 31 and jack 28

Referring now to FIG. 2, there is illustrated therein the main components of the Power Management System 1 used for a maximum volumetric efficiency, where the RF Receiving Antenna 3 is placed inside the hermetic titanium enclosure 4A of the Implanted Medical Device 4, rather than outside. Other than this simple difference, the Power Management System shown in FIG. 2 is identical to that of FIG. 1.

Figure 3:
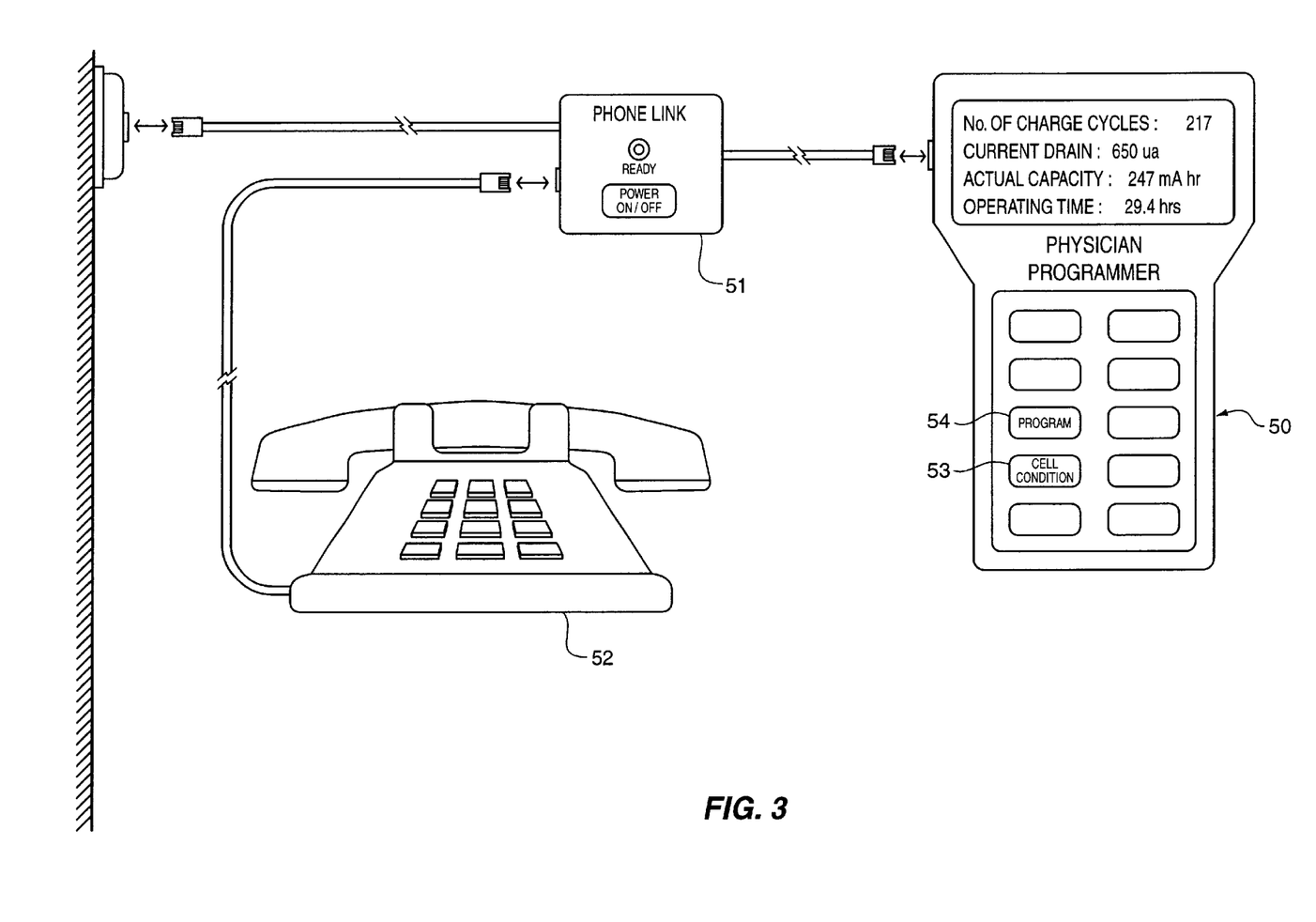
FIG. 3 is a block plan view of a physician programmer and a telephone link for communicating with the power management system shown in FIG. 1 or in FIG. 2.

Referring now to FIG. 3, the other side of the telephone link circuit is completed by using a "Physician Programmer" 50 which is connected, via another Phone Link coupler 51, to another telephone 52 having a connection established, via telephone 44 of FIG. 1, to the Charge Monitor 20 of FIG. 1.

By pressing push button 53, the physician or the manufacturer of the Implantable Medical Device 4 can retrieve data representing the condition of the rechargeable power source 10 and of the Implantable Medical Device 4.

By pressing push button 54, the physician can program new operating parameters values into the Implantable Medical Device 4. It should be obvious that the circuitry within the Phone Link 51 can be incorporated into the Physician Programmer 50 to accomplish the same goal.

Referring now to FIG. 4, there is illustrated therein a block schematic circuit diagram of the circuitry 8 for the Power Management Module 11 used to safely manage the charge and discharge cycles of the power source 10 powering the circuitry 8 of the Implantable Medical Device Circuit 4.

The following is a detailed narrative of the operation of each circuit component shown in FIG. 4.

Coupling RF Energy into the Implantable Medical Device

On the top-left side of FIG. 4, there is shown a RF Receiver 55 comprising the RF Receiving Antenna 2 used to pick-up the transmitted RF energy 5, capacitor 56 used for tuning the antenna 2 to the specific RF frequency to be transmitted, back-to-back Zener diodes 57 which are used to limit the maximum voltage that can develop across the antenna 2 in order to protect the charging circuit 60A comprising a Voltage Regulator 61 from over-voltage, a bridge 58 used for rectifying the RF energy into a DC voltage, and a capacitor 59 used for smoothing the output 60 of the bridge 58 to a steady DC voltage.

Operation of the RF Sensor

On the top-middle of FIG. 4, there is shown an RF Sensor 67 which is used to sense when the voltage at line 60 has risen above a preset voltage indicating that the level of RF energy 5 is sufficiently high to provide the current required to charge power source 10. When the voltage at line 60 reaches the reverse breakdown voltage of a Zener diode 68 connected as shown, sufficient voltage will develop at resistor 69 to turn on transistor 70, causing line 72 to switch low.

A microcontroller 100 detects this signal change and responds by switching line 85 high which turns on transistor 87 and connects the power source 10 to the common ground.

Controlling the Charge Rate Using a Closed-Loop Method

The Charge Rate Control 73 is used, under the supervision of microcontroller 100, to regulate the constant current value used to charge the power source 10. Microcontroller 100 applies a square wave at line 74 which is directed to the cathode of diode 75. During each negative half-cycle, diode 75 becomes forward biased and some charge is injected into capacitor 77 through resistor 76. However, during each positive half-cycle a smaller charge bleeds off from capacitor 77 through larger resistor 78 since diode 75 is reverse biased. The result is that a specific residual voltage develops at capacitor 77 due to the square wave at line 74. The specific voltage value depends on the frequency and duty cycle of the square wave and the resistance ratio between resistors 76 and 78. This residual voltage at line 82 drives transistor 79 in a constant current mode.

As transistor 79 sources current into the power source 10, a voltage will develop across resistor 81. This voltage is amplified by amplifier 83 and sampled by channel 4 of the A/D converter in micro-controller 100. Therefore, a closed-loop charging method is created where the charge rate is precisely regulated within a wide range by microcontroller 100. The charge rate is regulated by varying the frequency and/or duty cycle at line 74 until the desired current is measured by the A/D in the microcontroller 100. This closed-loop method permits adjusting the charging rate to the specific value recommended by each manufacturer of the power source 10, thus providing a universal charging method suitable for different types of power sources 10. This closed-loop method, also permits an initial fast charge rate in order to quickly reach the minimum operating voltage of the power source 10 of the Implantable Medical Device 4 to enable therapy, and then switch to a lower rate which is more benign to the life of the power source 10.

Also, since typically the Implantable Medical Device 4 incorporates a telemetry circuit to communicate with an external device, such as the Physician Programmer 50 of FIG. 3, the charge rate can be non-invasively changed after implant by down-loading new values via the Physician Programmer 50.

Switching to a Constant Voltage Mode to Top-Off the Cell

Once the power source 10 has reached a voltage close to its maximum rated voltage, charging is switched from constant current to constant voltage to preclude exceeding the maxim voltage recommended by the manufacturer. As an example, for a Lithium-Ion cell, the maximum value is typically 4.1 volts. For this example, microcontroller 100 will set the voltage regulator 61 to output 4.1 volts. Once the power source 10 has reached approximately 3.9 volts while charging at constant current, microcontroller 100 will fix line 74 high and line 64 low. This will turn off transistor 79 (constant current) and turn on transistor 65 (constant voltage), limiting the power source 10 to 4.1 volts when fully charged.

Disconnecting the Power Source to Avoid Deep Discharging

Microcontroller 100 incorporates a digital to analog converter having at least four channels: A/D1, A/D2, A/D3 and A/D4. A/D1 is used to monitor the voltage at the power source 10. During discharging of the power source 10, when the voltage at line 95 reaches a preset low value, microcontroller 100 will initiate the following power-down protocol:

1. Microcontroller 100 will signal the circuitry 8 of the Implantable Medical Device 4 to perform the necessary housekeeping chores to prepare for a power shut-down.
2. The microcontroller 100 will "float" the line 85 if no RF energy is being sensed by RF Sensor 67 (line 72 is high). This will turn off transistor 87, effectively disconnecting the power source 10 from the common ground. This is done to preclude damaging the power source 10 if allowed to be deeply discharged. Such will be the case for a Lithium-Ion cell. Note that the power is disconnected from the Power Management Module 11 and the circuitry 8 of the Implantable Medical Device 4, thus removing all loads from the power source 10.

Reconnecting the Power Source Upon Sensing the Transmission of RF Energy

As explained previously, RF Sensor 67 is used to sense when the level of RF energy 5 is sufficiently high to provide the current required to charge the power source 10. When adequate proximity and alignment is achieved between the charging antenna 6 and receiving antenna 2 (or 3) of FIG. 1 (or FIG. 2), line 72 will switch low, and in response, microcontroller 100 will switch line 85 high, reconnecting power source 10 to the common ground, and getting it ready for charging.

Disconnecting the Power Source Upon Sensing a High Temperature at the Power Source During Discharge On the bottom-right of FIG. 4, there is shown Temperature Sensor 98 whose output line 99 is connected to an A/D Converter channel A/D3. When the temperature of power source 10 is nearing an unsafe value which is a software loaded variable, microcontroller 100 will "float" line 104, switching off transistor 103. This effectively disconnects power source 10 from the circuitry 8 Implantable Medical Device 4. Note that the power source 10 will continue to power the microcontroller 100 (through the line 80, transistors 65 and the VDD supply) in order for the microcontroller 100 to sense when the temperature drops to a safe level by monitoring line 99.

Reconnecting the Power Source When the Temperature Drops to a Safe Level

When the temperature of the power source 10 drops to a safe level, microcontroller 100 will switch line 104 high which will turn on transistor 103, effectively reconnecting the power source 10 to the circuitry 8 of the Implantable Medical Device 4.

Measuring the Power Consumption of the Implantable Medical Device

On the center right of FIG. 4, there is shown the Current Measurement circuit 88 which comprises transistor 94 and its control line 93, voltage-dropping resistors 90 and 91, averaging capacitor 92, amplifier 89, and output line 96. As current is sourced into to the circuitry 8 of the Implantable Medical Device 4, a voltage drop will develop across the resistance path formed by resistors 90 and 91. This voltage drop is amplified by Amplifier 89 and directed to the A/D Converter channel A/D2 in microcontroller 100. Since Amplifier 89 has a gain of 100, if resistors 90 and 91 are assigned values of 1 and 9 Ohms, respectively, the voltage at line 96 will be 1 volt for a current drain of 10 mA (transistor 94 is switched on, shunting resistor 91). For lower current drains, microcontroller 100 will turn off transistor 94 to increase the voltage-dropping resistance to 10 Ohms. Therefore, high and low current drain scales are achieved. The circuitry 8 of the Implantable Medical Device 4 will communicate to microcontroller 100 the scale to be used depending on the parameter values presently being used by the Implantable Medical Device 4.

Measuring the Elapsed Time Since the Full Charge

On the top center of FIG. 4 there is shown microcontroller 100 which is also used to count the elapsed time since the last full charge. When the RF Transmitting Antenna 6 of FIG. 1 is removed from the RF Receiving antenna 2 (or 3 in FIG. 2), RF Sensor 67 will sense this event causing line 72 to switch high. Microcontroller 100 will sense the rise of line 72 and will start counting the elapsed time in days, hours and minutes, using a typical software timing loop known in the art.

Tracking the Capacity of the Power Source as the Charge/Discharge Cycles are Used Up The measured elapsed time from full charge to a full discharge in conjunction with the measured current drain, is used by microcontroller 100 to calculate the actual capacity of power source 10. Therefore, the capacity value is corrected for the fading effects caused by each charge/discharge cycle. Note: A full discharge refers to a power source discharged only to the lowest voltage recommended by the manufacturer of power source 10. In the case of a Lithium-Ion cell this low voltage is typically 3.0 volts.

Calculating the Operating Time of the Implantable Medical Device

The operating time from any point in the discharge curve of power source 10 to a full discharge, can be calculated by microcontroller 100 which measures (a) the average mA being consumed by the Implantable Medical Device 8, (b) the elapsed time since the last charge, and (b) the actual capacity of power source 10. The remaining operating time is calculated by: (1) multiplying the mA being consumed by the elapsed time in hours to arrive at the "consumed" capacity, (2) subtracting this "consumed" capacity from the "actual" (total) capacity to arrive at the "remaining" capacity, and (3) dividing the mA being consumed into the "remaining" capacity value of mA/hrs to arrive at the hours of operating time and dividing the answer by 24 to convert hours to days. Note that the power consumption of the Power Management Module 11 is insignificant (less than 3 uA) and therefore can be ignored in the calculation.

Figure 5:
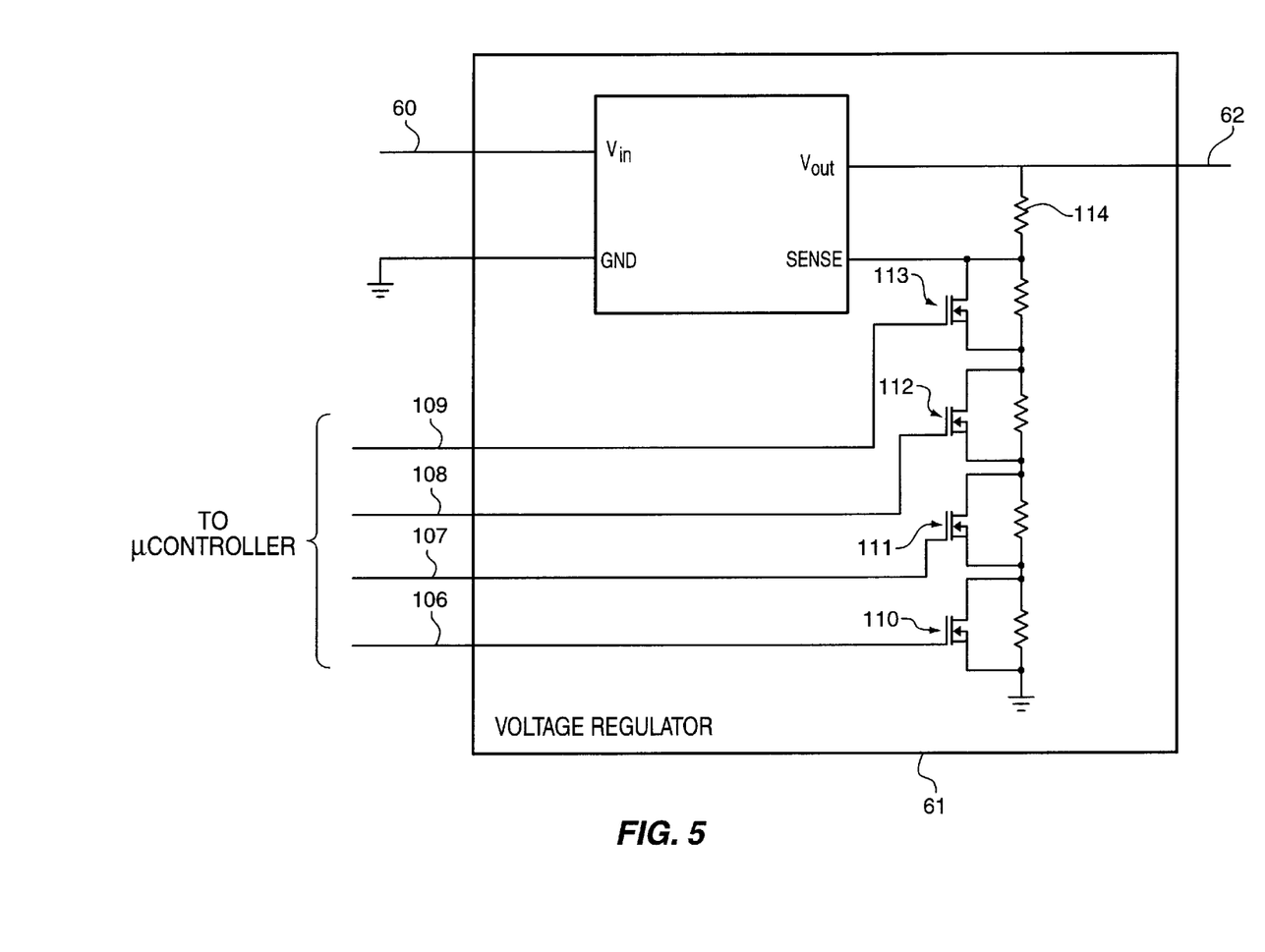
FIG. 5 is a block schematic circuit diagram for a voltage regulator having an output whose voltage value is adjusted by a bus.

Referring now to FIG. 5, there is illustrated therein a block schematic circuit diagram of the Voltage Regulator 61 with output 62 whose voltage value is adjusted by a bus 66. Microcontroller 100 controls the state of bus lines 106, 107, 108 and 109. These lines in turn control the state of transistors 110, 111, 112 and 113. These transistors are used to select the total value of resistance in the voltage sense loop for the voltage regulator 61. By adjusting the ratio of resistor 114 to the combined resistance of resistors 106, 107, 108 and 109, the output voltage of the voltage regulator 61 can be adjusted anywhere between 2.5 to 5.5 volts. This range covers the voltage required by most implantable grade, rechargeable power sources, including Lithium-Ion cell, Vanadium Oxide cell and a Super-capacitor.

From the foregoing description, it will be apparent that the method and system for power management of the present invention have a number of advantages, some of which have described above and others which are inherent in the invention. Also, it will be understood that modifications can be made to the method and system for power management of the present invention without departing from the teachings of the present invention. Accordingly, the scope of the invention is only to be limited as necessitated by the accompanying claims.

What is claimed is:

1. A method for managing power supplied from a charging circuit to a power source in an implantable medical device comprising the steps of:

(1) measuring and recording, each charge/discharge cycle of the power source, to obtain the corrected capacity of the power source in order to calculate and display, upon interrogation, the remaining operating time of the implanted device;

(2) providing within the implanted device circuitry for disconnecting the power source for preventing deep-discharging of the power source below safe limits upon reaching a pre-selected low voltage;

(3) providing circuitry for using variable constant current charge rates;

(4) providing circuitry for switching to constant voltage to top-off the power source at the completion of the charge cycle, in order to prevent overcharging beyond safe limits;

(5) providing circuitry for disconnecting the charging circuit from the power source within the implanted device upon the power source reaching a preselected high voltage level; and, (6) providing circuitry for full-time RF powered operation, in case of failure of the internal power source or for operation of the implanted medical device requiring extremely high power consumption instead of being powered from the internal power source of the implanted device.

2. The method of claim 1 including the step of: providing circuitry for transmitting to a remote receiver, via a telephone link, critical data that can be used by the physician and/or the device manufacturer to assess the performance and condition of the rechargeable power source and the implantable medical device.

3. The method of claim 1 including the step of: providing circuitry for transmitting to the implantable medical device, via a telephone link, new operation parameter value(s).

4. A method for managing power supplied from a charging circuit to a power source in an implantable medical device comprising the steps of:

detecting whether or not an RF sensor line has switched high or low;

controlling the charging rate;

non-invasively changing the charge high voltage limit;

switching to a constant voltage mode to top off the charge on the power source;

non-invasively changing the low voltage limit when the power source is disconnected during discharge;

disconnecting the power source when it reaches a low voltage limit;

reconnecting the power source upon sensing the transmission of RF energy;

disconnecting the power source upon sensing a high temperature;

reconnecting the power source when the temperature drops to a normal level;

measuring the power consumption of the circuitry for the implantable medical device;

measuring the elapsed time since the last full charge;

tracking the actual capacity of the power source; and, calculating the operating time left for the implantable medical device.

5. A method for managing power supplied from a charging circuit of a power management system to a power source in an implantable medical device comprising the steps of:

measuring the current drain of an implantable medical device;

measuring the elapsed time since the last full charge of a power source of the device;

calculating the actual capacity of the power source (corrected for fade) based on the variable of current drain and the variable of elapsed time;

calculating the operating time based on the variable of current drain and the variable of the actual capacity of the power source;

measuring the voltage of the power source;

signaling the implantable medical device when the power source voltage has reached a certain low value which requires disconnection from the power source;

disconnecting, during discharging, the power source from the implanted medical device upon the power source reaching a certain low voltage in order to prevent deep discharging of the power source and subsequent damage;

precisely limiting the charging voltage to the power source in order to prevent overcharging beyond safe limits;

disconnecting, during charging, the power source from the charging circuit upon the power source reaching a certain high voltage in order to prevent overcharging of the power source and subsequent damage;

sensing when the electromagnetic waves being transmitted by an RF transmitter/charger induce a voltage level above a certain value at an RF receiver of the implanted power management system;

reconnecting power supply inputs of the implanted medical device to the power source upon sensing this induced high voltage level;

monitoring the temperature of the power source during charging and discharging;

disconnecting the charging circuitry from the power source if the temperature of the power source raises above a certain level during charging;

reconnecting the charging circuitry to the power source when the temperature of the power source drops below a certain low value during charging;

disconnecting the implanted medical device from the power source if the temperature of the power source raises above a certain level during discharging; and, reconnecting the implantable medical device to the power source when the temperature of the power source drops below a certain low value during discharging.

6. The method of claim 5 including the step of: transmitting to a remote device, via a telephone link, data that can be used by one of a physician or a device manufacturer to assess the performance and condition of the rechargeable power source and the implantable medical device.

7. The method of claim 5 including the step of: transmitting, via a telephone link to, and setting in, the implantable medical device, new operational parameter value(s).

8. In a method for managing power supplied from a charging circuit of a power management system to a power source in an implantable medical device, the improvement comprising the step of: disconnecting, during discharging, the power source from the implanted medical device (a) upon the medical device having consumed a certain maximum capacity of ampere/hors and (b) the power source having reached a certain low voltage in order to prevent deep discharging of the power source and subsequent damage.

9. In a method for managing power supplied from a charging circuit of a power management system to a power source in an implantable medical device, the improvement comprising the steps of: (a) applying an initial precise charging voltage to the power source, (b) measuring the subsequent charging current and, (c) if the charging current exceeds a certain maximum level, modulating the charging voltage in order to maintain the charging current at a constant safe level in order to prevent overcharging beyond safe limits.

10. In a method for managing power supplied from a charging circuit of a power management system to a power source in an implantable medical device, the improvement comprising the steps of: (a) monitoring the voltage differential between the power source and the charging circuit and (b) disconnecting the charging circuit from the power source upon said voltage differential reaching a certain limit in order to prevent overcharging of the power source and subsequent damage.

11. A system for managing power supplied from a charging circuit to a power source in an implantable medical device comprising:

means for measuring and recording, each charge/discharge cycle of the power source, to obtain the corrected capacity of the power source in order to calculate and display, upon interrogation, the remaining operating time of the implanted device;

circuitry for disconnecting the power source for preventing deep-discharging of the power source below safe limits upon reaching a pre-selected low voltage;

circuitry for using variable constant current charge rates;

circuitry for switching to constant voltage to top-off the power source at the completion of the charge cycle, in order to prevent overcharging beyond safe limits;

circuitry for disconnecting the charging circuit from the power source within the implanted device upon the power source reaching a preselected high voltage level; and, circuitry for full-time RF powered operation, in case of failure of the internal power source or for operation of the implanted medical device requiring extremely high power consumption instead of being powered from the internal power source of the implanted device.

12. The system of claim 11 including: circuitry for transmitting to a remote receiver, via a telephone link, critical data that can be used by the physician and/or the device manufacturer to assess the performance and condition of the rechargeable power source and the implantable medical device.

13. The system of claim 11 including: circuitry for transmitting to the implantable medical device, via a telephone link, new operation parameter value(s).

14. A system for managing power supplied from a charging circuit to a power source in an implantable medical device comprising:

means for detecting whether or not an RF sensor line has switched high or low;

means for controlling the charging rate;

means for non-invasively changing the charge high voltage limit;

means for switching to a constant voltage mode to top off the charge on the power source;

means for non-invasively changing the low voltage limit when the power source is disconnected during discharge;

means for disconnecting the power source when it reaches a low voltage limit;

means for reconnecting the power source upon sensing the transmission of RF energy;

means for disconnecting the power source upon sensing a high temperature;

means for reconnecting the power source when the temperature drops to a normal level;

means for measuring the power consumption of the circuitry for the implantable medical device;

means for measuring the elapsed time since the last full charge;

means for tracking the actual capacity of the power source; and, means for calculating the operating time left for the implantable medical device.

15. A system for managing power supplied from a charging circuit of a power management system to a power source in an implantable medical device comprising:

means for measuring the current drain of an implantable medical device;

means for measuring the elapsed time since the last full charge of a power source of the device;

means for calculating the actual capacity of the power source (corrected for fade) based on the variable of current drain and the variable of elapsed time;

means for calculating the operating time based on the variable of current drain and the variable of the actual capacity of the power source;

means for measuring the voltage of the power source;

means for signaling the implantable medical device when the power source voltage has reached a certain low value which requires disconnection from the power source;

means for disconnecting, during discharging, the power source from the implanted medical device upon the power source reaching a certain low voltage in order to prevent deep discharging of the power source and subsequent damage;

means for precisely limiting the charging voltage to the power source in order to prevent overcharging beyond safe limits; means for disconnecting, during charging, the power source from the charging circuit upon the power source reaching a certain high voltage in order to prevent overcharging of the power source and subsequent damage;

means for sensing when the electromagnetic waves being transmitted by an RF transmitter/charger induce a voltage level above a certain value at an RF receiver of the implanted power management system;

means for reconnecting power supply inputs of the implanted medical device to the power source upon sensing this induced high voltage level;

means for monitoring the temperature of the power source during charging and discharging;

means for disconnecting the charging circuitry from the power source if the temperature of the power source raises above a certain level during charging;

means for reconnecting the charging circuitry to the power source when the temperature of the power source drops below a certain low value during charging;

means for disconnecting the implanted medical device from the power source if the temperature of the power source raises above a certain level during discharging; and, means for reconnecting the implantable medical device to the power source when the temperature of the power source drops below a certain low value during discharging.

16. The system of claim 15 including: means for transmitting to a remote device, via a telephone link, data that can be used by one of a physician or a device manufacturer to assess the performance and condition of the rechargeable power source and the implantable medical device.

17. The system of claim 15 including: means for transmitting, via a telephone link to, and setting in, the implantable medical device, new operational parameter value(s).

18. In a system for managing power supplied from a charging circuit of a power management system to a power source in an implantable medical device, the improvement comprising: means for disconnecting, during discharging, the power source from the implanted medical device (a) upon the medical device having consumed a certain maximum capacity of ampere/hours and (b) the power source having reached a certain low voltage in order to prevent deep discharging of the power source and subsequent damage.

19. In a system for managing power supplied from a charging circuit of a power management system to a power source in an implantable medical device, the improvement comprising: means for precisely limiting the charging voltage to the power source, means for measuring the subsequent charging current and, means for modulating the charging voltage, if the charging current exceeds a certain maximum level, in order to maintain the charging current at a constant safe level in order to prevent overcharging beyond safe limits.

20. In a system for managing power supplied from a charging circuit of a power management system to a power source in an implantable medical device, the improvement comprising: means for monitoring the voltage differential between the power source and the charging circuit and means for disconnecting the charging circuit from the power source upon said voltage differential reaching a certain limit in order to prevent overcharging of the power source and subsequent damage.

21. A method for managing the power supply to a power source of an implantable medical device comprising the steps of:

(a) providing within the implanted device circuitry for disconnecting the power source for preventing deep-discharging of the power source below safe limits upon reaching a pre-selected low voltage;

(b) providing circuitry for switching to constant voltage to top-off the power source at the completion of the charge cycle, in order to prevent overcharging beyond safe limits;

(c) providing circuitry for disconnecting the charging circuit from the power source within the implanted device upon the power source reaching a preselected high voltage level; and (d) providing circuitry for full-time RF powered operation, in case of failure of the internal power source or for operation of the implanted medical device requiring extremely high power consumption instead of being powered from the internal power source of the implanted device.

22. A system for managing power supplied from a charging circuit to a power source in an implantable medical device comprising:

(a) circuitry within the implanted device for disconnecting the power source for preventing deep-discharging of the power source below safe limits upon reaching a preselected low voltage;

(b) circuitry for switching to constant voltage to top-off the power source at the completion of the charge cycle, in order to prevent overcharging beyond safe limits;

(c) circuitry for disconnecting the charging circuit from the power source within the implanted device upon the power source reaching a preselected high voltage level; and (d) circuitry for full-time RF powered operation, in case of failure of the internal power source or for operation of the implanted medical device requiring extremely high power consumption instead of being powered from the internal power source of the implanted device.

* * * * *